US009427173B2

(12) United States Patent
Sirohey et al.

(10) Patent No.: US 9,427,173 B2
(45) Date of Patent: Aug. 30, 2016

(54) DETERMINING MECHANICAL FORCE ON ANEURYSMS FROM A FLUID DYNAMIC MODEL DRIVEN BY VESSEL BLOOD FLOW INFORMATION

(75) Inventors: Saad Ahmed Sirohey, Pewaukee, WI (US); Paul E. Licato, Milwaukee, WI (US); Gopal B. Avinash, Menomonee Falls, WI (US); Tamanna N. Bembenek, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 2009 days.

(21) Appl. No.: 12/118,628

(22) Filed: May 9, 2008

(65) Prior Publication Data

US 2009/0281423 A1 Nov. 12, 2009

(51) Int. Cl.
| | |
|---|---|
| *A61B 5/05* | (2006.01) |
| *A61B 5/107* | (2006.01) |
| *A61B 5/02* | (2006.01) |
| *A61B 6/03* | (2006.01) |
| *A61B 6/00* | (2006.01) |
| *G06F 19/00* | (2011.01) |
| *G06T 7/00* | (2006.01) |
| *G06T 15/08* | (2011.01) |

(52) U.S. Cl.
CPC ......... *A61B 5/1075* (2013.01); *A61B 5/02007* (2013.01); *A61B 6/032* (2013.01); *A61B 6/481* (2013.01); *A61B 6/504* (2013.01); *G06F 19/321* (2013.01); *G06F 19/345* (2013.01); *G06F 19/3437* (2013.01); *G06T 7/0012* (2013.01); *G06T 15/08* (2013.01); *G06T 2207/10081* (2013.01); *G06T 2207/10088* (2013.01); *G06T 2207/30101* (2013.01)

(58) Field of Classification Search
USPC ......... 600/407, 431, 437, 410; 382/126, 130
See application file for complete search history.

(56) References Cited

U.S. PATENT DOCUMENTS

| | | | | |
|---|---|---|---|---|
| 6,500,118 | B1* | 12/2002 | Hashimoto | ............... 600/437 |
| 7,015,907 | B2 | 3/2006 | Tek et al. | |
| 2005/0187461 | A1* | 8/2005 | Murphy et al. | ............ 600/416 |
| 2006/0149522 | A1* | 7/2006 | Tang | ........................... 703/11 |
| 2008/0294038 | A1* | 11/2008 | Weese et al. | ............. 600/431 |

OTHER PUBLICATIONS

Will Schroeder, Ken Martin and Bill Lorensen, The Visualization Toolkit, An Object-Oriented Approach to 3D Graphics, ISBN 0131998374, Prentice-Hall 1996.
Cebral JR, Hernandez M, Frangi AF, et al. Subject-specific modeling of intracranial aneurysms. Proc SPIE Med Imaging 2004;5369:319-327.
M. Hernandez, A.F. Frangi, Brain aneurysm segmentation in CTA and 3DRA using geodesic active regions based on second order prototype features and non parametric density estimation. SPIE Medical Imaging 2005: Physiology, Function, and Structure from Medical Images. vol. 5747, p. 514-525; retrieved from the Internet on May 9, 2008 from www.harvard.edu.

(Continued)

*Primary Examiner* — Joel F Brutus
(74) *Attorney, Agent, or Firm* — Dean D. Small; The Small Patent Law Group, LLC

(57) ABSTRACT

Systems, methods and apparatus are provided through which in some implementations changes in an aneurysm in a patient over time are identified by determining temporal differences between segmented aneurysms in a plurality of longitudinal exams and visually presenting the temporal differences.

19 Claims, 15 Drawing Sheets

(56) References Cited

OTHER PUBLICATIONS

GE Healthcare, Product Technology Case study, retrieved from the Internet on Feb. 25, 2008 from http://www.gehealthcare.com/euen/ct/products/products_technologies/products/lightspeed-vct-xt/26552_VCT_XT_05_shuttle-clinical-case.html.

Ursula Gordon, Numerical Simulation of Blood Flow in the Basilar Artery under Non-Steady Flow Conditions.

Hidetaka Arimura, Automated Computerized Scheme for Detection of Unruptured Intracranial Aneurysms in Three-dimensional Magnetic Resonance Angiography, Acad Radiol. Oct. 2004;11(10):1093-104.

Yick Lee, Hemodynamics of a cerebral aneurysm model, California Engineer, vol. 84 Issue 03: Spring 2006, retrieved from the Internet on Apr. 28, 2008 from http://caleng.berkeley.edu/archive/84.3-spring2006/hemodynamics.pdf.

Masayuki, Predicting Hemorrhage, Japan Journal, Mar. 2006, retrieved from the Internet on Apr. 28, 2008 from http://www.japanjournal.jp/tjje/show_art.php?INDyear=06&INDmon=03&artid=fb7603d50766da9a82f20ef268b6388f&page=3.

Marie Oshima, Biosimulation and visualization: effect of cerebrovascular geometry on hemodynamics, Ann N Y Acad Sci. Oct. 2002; 972:337-44, retrieved from the Internet on Apr. 28, 2008 from www.annalsnyas.org/cgi/content/full/972/1/337/T149?ck=nck.

Oshima Laboratory, Stereoscopic PIV measurement in cerebral artery model with rigid wall, retrieved from the Internet on Apr. 28, 2008 from http://www.oshimalab.iis.u-tokyo.ac.jp/olab3/Res_Exp_aneurism_eng.html.

Masaaki Shojima, Magnitude and Role of Wall Shear Stress on Cerebral Aneurysm; Computational Fluid Dynamic Study of 20 Middle Cerebral Artery Aneurysms, Stroke. 2004;35:2500-2505.

\* cited by examiner

FIG. 13     1300

DETERMINING MECHANICAL FORCE ON ANEURYSMS FROM A FLUID DYNAMIC MODEL DRIVEN BY VESSEL BLOOD FLOW INFORMATION

RELATED APPLICATION

This application is related to U.S. application Ser. No. 12/118,616, filed May 9, 2008 (now U.S. Pat. No. 8,116,542, issued Feb. 14, 2012) entitled "DETERMINING HAZARD OF AN ANEURYSM BY CHANGE DETERMINATION."

FIELD

This invention relates generally to angiography, and more particularly to imaging of aneurysms.

BACKGROUND

Aneurysms are a fundamental cause of hemorrhagic stroke involving 20% of all stroke cases. In aneurysm ruptures, a portion of the brain is filled blood that can cause tissue death or pressure in the head. Large hemorrhages can be fatal and are cause by clearly visible large aneurysm. A particular case of interest is the debilitating "dementia" like conditions caused by micro hemorrhages that due to small aneurysms ruptures.

Aneurysms are infrequently encountered on a straight, non-branching segment of an intracranial artery. The aneurysms occurring on straight, non-branching segments are more often found to have sacs that point longitudinally along the wall of the artery in the direction of blood flow and to project only minimally above the adventitial surface. Aneurysms having these characteristics are of a dissecting type, rather than of the congenital saccular type, and development of dissecting type aneurysms is heralded more frequently by the onset of ischemic neurological deficits than by the subarachnoid hemorrhage associated with congenital saccular aneurysms.

Detecting small aneurysms is particularly difficult for CTA exams as these are very minute and are often indistinguishable from the vasculature. Additionally, the presence of bone in the skull causes added difficulty to visualize these structures.

BRIEF DESCRIPTION

In one aspect, the hazard of an aneurysm is measured by determining changes, and by determining a rate of change, of an aneurysm in longitudinal exams using automated segmentation and quantification tools.

In another aspect, a method to image a patient includes determining mechanical force attributes on a wall of aneurism using a fluid dynamics model and visually presenting the determined mechanical force attributes in three-dimensional rendition of the volumetric data using visual cues to indicate degree of mechanical force attributes.

In yet another aspect, a method to image a patient includes accessing four-dimensional image data that tracks contrast flow through a vasculature, determining vessel flow information of the vasculature, determining a mechanical force attributes on a wall of an aneurism from the vessel flow information using a fluid dynamics model wherein the mechanical force attributes varies in proportion to velocity of fluid in vasculature in a direction perpendicular to a plane of shear in the vasculature, visually presenting the determined mechanical force attributes in three-dimensional rendition of the volumetric data using visual cues to indicate degree of mechanical force attributes.

In yet a further aspect, A medical imaging system includes a processor, a storage device coupled to the processor and software apparatus operable on the processor including a fluids dynamics model, a vessel flow analyzer that is operable to determine vessel flow data of a vasculature represented in four-dimensional image data, a mechanical force analyzer that is operable to determine mechanical force attributes on a wall of a aneurism from the vessel flow data using the fluid dynamics model wherein the mechanical force attributes varies in proportion to a velocity of a fluid in the vasculature in a direction perpendicular to a plane of shear in the vasculature.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into four sections. In the first section, a system level overview is described. In the second section, implementations of methods are described. In the third section, particular implementations are described. Finally, in the fourth section, a conclusion of the detailed description is provided.

System Level Overview

The systems in this section describe a workflow in which longitudinal exams are used to assess the seriousness of the aneurysm in either computed tomography angiography (CTA) and/or magnetic resonance (MRA).

Figure 1:
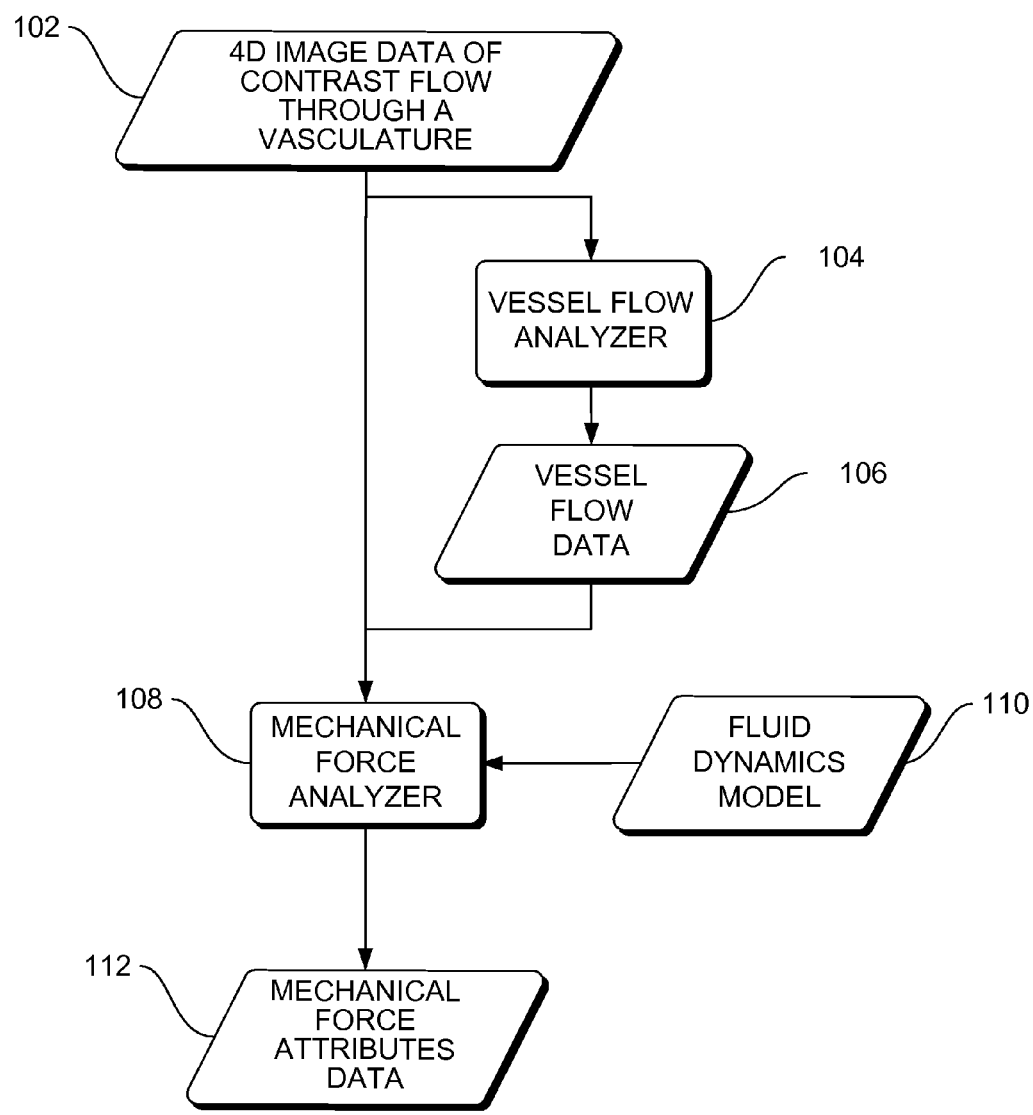
FIG. 1 is a block diagram of an overview of a system to determine changes of an anatomical structure in a patient over time, according to an implementation.

FIG. 1 is a block diagram of an overview of a system 100 to determine changes of an anatomical structure in a patient over time, according to an implementation. System 100 determines and/or identifies mechanical force attributes of a vasculature represented in four-dimensional images of flow through the vasculature.

System 100 includes a vessel flow analyzer 104 that is operable to determine vessel flow 106 of a vasculature from four-dimensional (4D) image data 102. In some embodiment, the 4D image data is computed-tomography data that is acquired using a cine dynamic imaging system or a GE shuttle mode (moving the patient to and fro in order to expand image coverage) to acquire a time series of a contrast bolus passing through the tissue of interest. The expanded coverage to 8 centimeter (CM) or more provides an image size in which a sufficient portion of the vasculature of the brain can be imaged in 4D. The contrast uptake in time in any of the arterial vessels allows for the computation of flow.

In some implementations of cerebral aneurysms, the vessel flow is determined using the volumetric dynamic data (4D) that is tracking the contrast bolus through the neuron vasculature. The first part of the method identifies two locations on a vessel (d1 and d2) that are a defined distance apart. The points on the vessel are identified at a time when the vessel is fully perfused with the contrast. Since the head is a rigid body and the motion in the vessels is primarily pulsatory due to the heartbeat these landmarks can be easily backtracked in time to a stage when there is no contrast in the vessel. The method of determining the flow in the vessel is to determine the times t1 and t2 when the two landmark points on the vessel reach a steady state contrast enhanced value. The velocity of the fluid is determined by dividing the distance between the points by the time the fluid takes for the contrast to traverse that distance, as follows in equation 1:

$$F = V * A \qquad \text{Equation 1}$$

where $$V = \frac{d2 - d1}{t2 - t1}$$

In Equation 1, F represents the flow, V represents velocity and A represents the cross sectional area of the vessel.

System 100 also includes a mechanical force analyzer 108 that is operable to determine mechanical force attributes 112 on a wall of an aneurism. In some implementations, the mechanical force analyzer 108 determines the data representing mechanical force attributes 112 from the vessel flow data 106 using a fluid dynamics model 110.

In some implementations, the mechanical force attributes 112 vary in proportion to a velocity of a fluid in the vasculature in a direction perpendicular to a plane of shear in the vasculature.

In some implementations, the fluid dynamics model 110 includes a Navier-Stokes fluid dynamics model, as follows:

$$\rho \frac{Dv}{Dt} = \nabla \cdot \mathbb{P} + \rho f \qquad \text{Equation 2}$$

In equation 2, $\rho$ represents the fluid density, $D/D_t$ represents a substantive derivative (also called the material derivative), V represents a velocity vector, f represents a body force vector, $\mathbb{P}$ represents a tensor that represents the surface forces applied on a fluid particle (the comoving stress tensor). The substantive derivative is a derivative taken with respect to a coordinate system moving with velocity U.

Unless the fluid is made up of spinning degrees of freedom like vortices, $\mathbb{P}$ is a symmetric tensor. In general, (in three dimensions) $\mathbb{P}$ has the form:

$$\mathbb{P} = \begin{pmatrix} \sigma_{xx} & \tau_{xy} & \tau_{xz} \\ \tau_{yx} & \sigma_{yy} & \tau_{yz} \\ \tau_{zx} & \tau_{xy} & \sigma_{zz} \end{pmatrix} \qquad \text{Equation 3}$$

In equation 3, $\sigma$ represents normal stresses, and $\tau$ represents tangential stresses (shear stresses). Equation 3 is a set of three equations, one per dimension. By themselves, the three equations of equation 3 are insufficient to produce a solution. However, adding conservation of mass and appropriate boundary conditions to the system of equations produces a solvable set of equations.

Or using the Newtonian fluid modeling whose shear stress is linearly proportional to the velocity gradient in the direction perpendicular to the plane of shear. This definition means regardless of the forces acting on a fluid, the fluid continues to flow. For example, water is a Newtonian fluid, because the fluid continues to display fluid properties no matter how much the fluid is stirred or mixed. A slightly less rigorous definition is that the drag of a small object being moved through the fluid is proportional to the force applied to the object.

In equations for a Newtonian fluid, the constant of proportionality between the shear stress and the velocity gradient is known as the viscosity. A simple equation to describe Newtonian fluid behaviour follows:

$$\tau = \mu \frac{dv}{dx} \qquad \text{Equation 4}$$

In equation 4, τ represents shear stress exerted by the fluid ("drag"), μ represents the fluid viscosity, a constant of proportionality, $D_V/D_X$ represents the velocity gradient perpendicular to the direction of shear.

For a Newtonian fluid, the viscosity, by definition, depends only on temperature and pressure, not on the forces acting upon it. If the fluid is incompressible and viscosity is constant across the fluid, the equation governing the shear stress (in Cartesian coordinates) follows:

$$\tau_{ij} = \mu \left( \frac{\partial v_i}{\partial x_j} + \frac{\partial v_j}{\partial x_i} \right) \quad \text{Equation 5}$$

In equation 5, $\tau_{ij}$ represents the shear stress on the $i^{th}$ face of a fluid element in the $j^{th}$ direction $v_i$ represents the velocity in the $i^{th}$ direction, $x_j$ represents the $j^{th}$ direction coordinate. If a fluid does not obey this relation, the fluid is termed a non-Newtonian fluid, of which there are several types.

Figure 2:
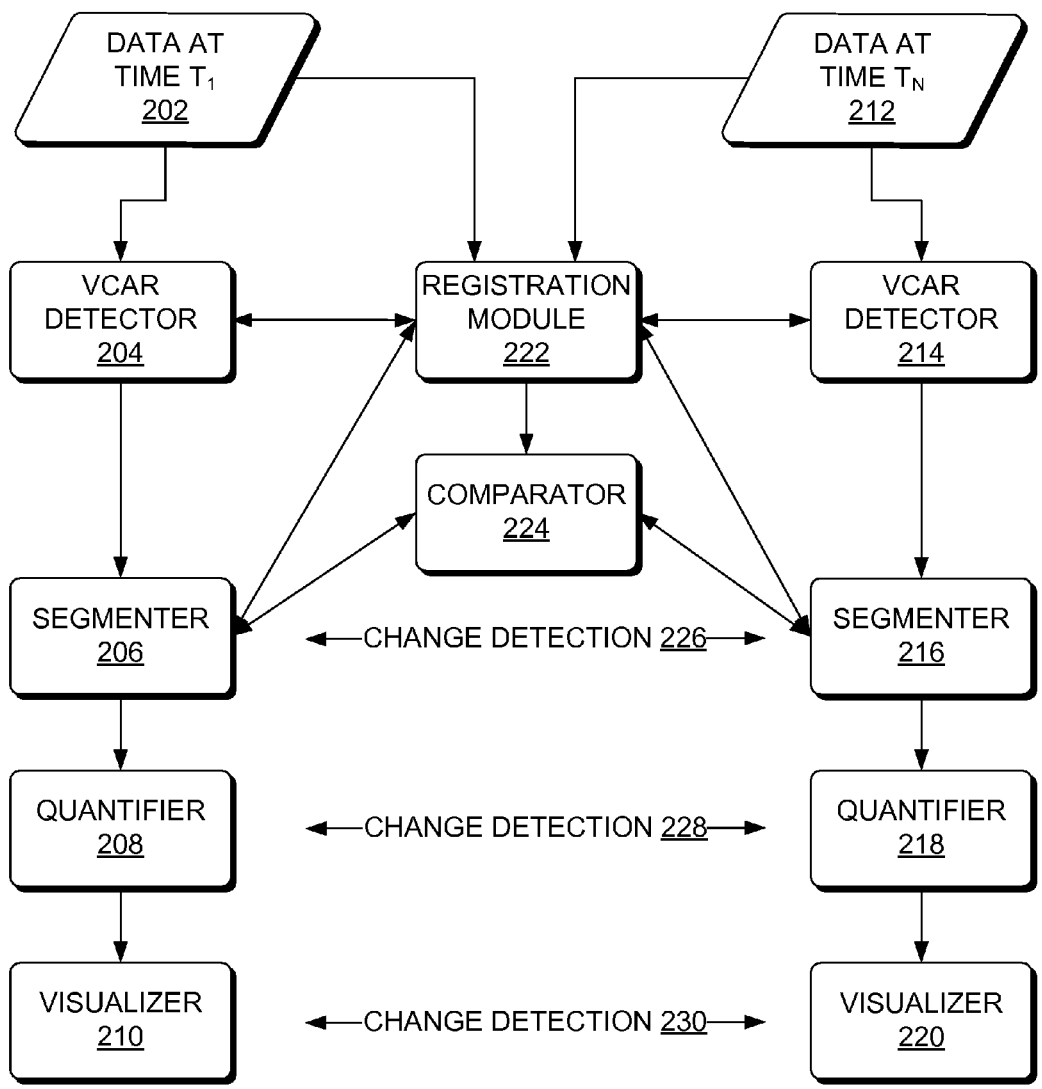
FIG. 2 is a block diagram of an overview of a system to determine changes of an anatomical structure in a patient over time, according to an implementation.

FIG. 2 is a block diagram of an overview of a system 200 to determine changes of an anatomical structure in a patient over time, according to an implementation. System 200 provide acquisition storage of longitudinal images, segmentation of the images, and registration, comparison and reporting of results. FIG. 2 shows many different combinations of dataflow as indicated by bi-directional arrows.

System 200 includes a first image 202. The first image 202 is acquired at a particular time, $T_1$.

A volume computer-assisted reading (VCAR) detector 204 is operable to receive the first image 202, perform pre-segmentation and temporal analysis on the image and transmit the first image 202 to a segmenter 206.

More specifically, the segmentation performed by the VCAR detector 204 includes pre-segmentation. Pre-segmentation ensures that unwanted dominating structures in the image data are not included in the subsequent processing tasks. Examples of dominating structures may include bone structures obscuring blood vessels and aneurysms, tagged materials obscuring the presence of polyps in colonography, cardiac chambers obscuring the coronary vessel tree visualization etc.

In many cases, one may remove the dominating unwanted structure obscuring salient features and proceed with subsequent processing steps. Alternatively, a mask corresponding to the dominating unwanted structure may be extracted and used in the subsequent processing steps.

VCAR detector 204 is also capable of detecting an aneurysm: The first step in detecting an aneurysm is shape detection, which is described in greater detail in FIG. 9 below. Even though only spherical shape detection is described in FIG. 9, the general method can be applicable to other shapes and texture detection.

A subsequent step performed by the VCAR detector 204 is extraction of the detected shape(s) which reduces the overlap of the disparate responses by using a-priori anatomical information. For the illustrative example of the vascular aneurysm three-dimensional (3D) responses are determined using formulation using local curvature at implicit isosurfaces. The method termed curvature tensor determines the local curvatures Kmin and Kmax in the null space of the gradient. The respective curvatures can be determined using the following equation:

$$k_i = (\min \hat{v}, \max \hat{v}) \frac{-\hat{v}^T N^T H N \hat{v}}{\|\nabla I\|} \quad \text{Equation 6}$$

Equation 6

In equation 6, k represents a curvature, v represents a vector in the N null space of the gradient of image data I with H being a Hessian of image I. The solution to equation 6 are the eigen values of the following equation:

$$\frac{-N^T H N}{\|\nabla I\|} \quad \text{Equation 7}$$

In equation 7, responses of the curvature tensor (Kmin and Kmax) are segregated into spherical and cylindrical responses based on thresholds on Kmin, Kmax and the ratio of Kmin/Kmax derived from the size and aspect ratio of the sphericalness and cylindricalness that is of interest, in one exemplary formulation the aspect ratio of 2:1 and a minimum spherical diameter of 1 mm with a maximum of 20 mm is used. It should be noted that a different combination would result in a different shape response characteristic that would be applicable for a different anatomical object.

The disparate responses so established do have overlapping regions that can be termed as false responses. The differing acquisition parameters and recon process and noise characteristics of the recon process are a major source of these false responses. A method of removing the false responses is adjusting the threshold values to compensate for the differing acquisitions. The adjusting includes creating a mapping of the thresholds to all possible acquisition. Mapping the thresholds includes utilizing anatomical information in the form of the scale of the responses on large vessels (cylindrical responses) and the intentional biasing of the response towards spherical vs. cylindrical to come up with the use of morphological closing of the cylindrical response volume to cull any spherical responses that are in the intersection of the "closed" cylindrical responses and the spherical response. An exemplary response is shown in FIG. 2.

In general, the segmenter 206 is operable to segment an aneurysm in the image 202. The segmenter 206 provides automated or manual means for isolating regions of interest. In many cases of practical interest, the entire image can be the region of interest. After an object is detected, a region of interest (ROI) needs to be extracted to calculate features in the data. This step is application dependent. Several techniques or combinations of techniques can be used for this purpose including but not limited to iterative adaptive thresholding, k-means segmentation, edge detection, edge linking, curve fitting, curve smoothing, 2D/3D morphological filtering, region growing, fuzzy clustering, image/volume measurements, heuristics, knowledge-based rules, decision trees, neural networks. The segmentation of the region of interest can be performed either manually and/or automatically. The manual segmentation involves displaying the data and a user delineating the region using a mouse or any other suitable interface (e.g. touch screen, eye-tracking, voice commands). An automated segmentation algorithm can use prior knowledge such as the shape and size of a mass to automatically delineate the area of interest. A semi-automated method which is the combination of the above two methods may also be used.

A quantifier 208 is operable to receive the segmented image and to quantify the segmented aneurysm in the image 202.

A visualizer 210 is operable to visualize the segmented aneurysm. The visualizer 210 module provides the display and quantification capabilities for the user to visualize and or quantify the results of temporal comparison. In practice, one can use all the available temporal image-pairs for the analysis. The comparison results can be displayed in many ways, including textual reporting of quantitative comparisons, simultaneous overlaid display with current or previous images using a logical operator based on some pre-specified criterion, color look-up tables can be used to quantitatively display the comparison, or two-dimensional or three-dimensional cine-loops can be used to display the progression of change for image to image. The resultant image can also be coupled with an automated or manual pattern recognition technique to perform further qualitative and/or quantitative analysis of the comparative results. The results of this further analysis can be display alone or in conjunction with the acquired images using any of the methods described above.

In some implementations, visualizer 210 performs volume rendering which provide visualization of three-dimensional data. Volume rendering is a technique of visualizing sampled functions of three spatial dimensions by computing 2-D projections of a semitransparent volume.

Currently, a major application area of volume rendering is medical imaging, where volume data is available from X-ray Computed Tomography (CT) scanners. CT scanners produce three-dimensional stacks of parallel plane images, each of which consist of an array of X-ray absorption coefficients. Typically X-ray CT images will have a resolution of 512*512*12 bits and there will be up to 500 slices in a stack. In the two-dimensional domain, these slices can be viewed one at a time. The advantage of CT images over conventional X-ray images is that CT images only contain information from that one plane. A conventional X-ray image, on the other hand, contains information from all the planes, and the result is an accumulation of shadows that are a function of the density of the tissue, bone, organs, etc., anything that absorbs the X-rays. The availability of the stacks of parallel data produced by CT scanners prompted the development of techniques for viewing the data as a three-dimensional field rather than as individual planes. This gave the immediate advantage that the information can be viewed from any viewpoint.

Rendering techniques include rendering voxels in binary partitioned space, marching cubes, and ray casting. In regards to rendering voxels in binary partitioned space, choices are made for the entire voxel, which can produce a "blocky" image. In regards to marching cubes reduces the blocky aspect, but causes some other problems. In regards to ray casting, the best use of the three-dimensional data is provided without an attempt to impose any geometric structure on the three-dimensional data. Ray casting solves one of the most important limitations of surface extraction techniques, namely the way in which ray casting displays a projection of a thin shell in the acquisition space. Surface extraction techniques fail to take into account that, particularly in medical imaging, data may originate from fluid and other materials, which may be partially transparent and should be modeled as such, of which ray casting does not suffer.

Other types of visualization include virtual reality, virtual examination, immersive visualization, multiple image fusion, synchronized viewing in multiple view ports (4D/4D, 4D/3D, 4D/2D, 4D/1D, 4D/0D, 3D/3D, 3D/2D, 3D/1D, 3D/0D, 2D/2D, 2D/1D, 2D/0D), overlay visualization (text, symbol, feature, texture, color, shape, indicator, combination) etc.

System 200 includes a second image 212. The second image 212 was acquired at a particular time, $T_1$. A volume computer-assisted reading (VCAR) detector 214 is operable to receive the second image 212 and transmit the second image 212 to a segmenter 216. The VCAR detector 214 is operable to perform the same functions as the VCAR detector 204. The segmenter 216 is operable to segment an aneurysm in the image 212. A quantifier 218 is aorta at the circuit and operable to receive the segmented image and to quantify the segmented aneurysm in the image 212. A visualizer 211 is operable to visualize the segmented aneurysm. In some implementations, the segmenter 206, the quantifier 208, and the visualizer 210 are the same component as the segmenter 216, the quantifier 218 and a visualizer 220, respectively.

A registration module 222 module provides methods of registration. If the regions of interest for temporal change analysis are small, rigid body registration transformations including translation, rotation, magnification, and shearing may be sufficient to register a pair of images from S1 and S2. However, if the regions of interest are large including almost the entire image, warped, elastic transformations usually have to be applied. One way to implement the warped registration is to use a multi-scale, multi-region, pyramidal approach. In this approach, a different cost function highlighting changes may be optimized at every scale. An image is resampled at a given scale, and then the image is divided into multiple regions. Separate shift vectors are calculated at different regions. Shift vectors are interpolated to produce a smooth shift transformation, which is applied to warp the image. The image is resampled and the warped registration process is repeated at the next higher scale until the predetermined final scale is reached. Other methods of registration can be substituted here as well. Some of the well-known techniques involve registering based on the mutual information histograms. These methods are robust enough to register anatomic and functional images. For the case of single modality anatomic registration, we prefer the method described above where as for the single modality functional registration, we prefer to use mutual information histograms.

The registration module 222 is also operable to propagate a location of an aneurysm from the first image 202 onto a second image 212.

The VCAR detector 204 is operable to process registration information associated with each of the plurality of images.

A temporal comparator 224 is operable to identify changes in the detected aneurism. In particular, the temporal comparator 224 is operable to identify changes in the segmented portions of the two images 202 and 212. The temporal comparator 224 is also operable to identify changes in the quantifications of the segmented aneurysms. The temporal comparator 124 is also operable to identify changes in the visualizations of the segmented aneurysms. It should be noted that even though temporal VCAR with respect an aneurysm VCAR is described, the generic methodology can be expanded to temporal processing of any VCAR process.

Some implementations of the temporal comparator 224 includes a variety of different methods for comparing temporally separated anatomical parts, these include; comparison after quantification has been done, e.g. comparing the change in volume of a lesion or aneurysm, comparison from a visual point of view e.g. comparing the shape and size of a anatomical part to assess any change in a qualitative manner, comparison of bookmarked locations (and acceptance/rejection of the bookmarked locations) e.g. validating the registration module by verifying that the bookmarks have propagated to the right anatomical location in the two exams. In addition computational comparisons can also be performed to improve the conspicuity of change e.g. for mono-modality temporal processing, the prior art methods obtain difference image $D1_a=(S1*S2)/(S2*S2+\Phi)$, where the scalar constant $\Phi>0$. In the degenerative case of which $\Phi=0$ is not included here, the above equation becomes a straightforward division, S1/S2.

While the system 200 is not limited to any particular images 202 and 212, VCAR detectors 204 and 214, segmenters 206 and 216, quantifiers 208 and 218, and visualizers 210 and 220, registration module 222, comparator 224, segmentation change detector 226, quantification change detector 228, and visualization change picture 230, for sake of clarity a simplified images 202 and 212, VCAR detectors 204 and 214, segmenters 206 and 216, quantifiers 208 and 218, and visualizers 210 and 220, registration module 222, comparator 224, segmentation change detector 226, quantification change detector 228, and visualization change picture 230 are described.

In applications of system 200, the data collected at $t_{n-1}$ and $t_0$ can be processed in different ways as shown in FIG. 2. First method involves performing independent VCAR operations on each of the data sets and performing the comparison analysis on the final outputs visually. Second method involves merging the results prior to the segmentation step. Third method involves registering data prior to feature identification step. Fourth method proposed involves a combination of the above methods. Additionally, the proposed method also includes a step to register images to the same coordinate system. Optionally, image comparison results following registration of two data sets can also be the additional input to the segmentation step. Thus, the proposed method leverages temporal differences and feature commonalities to arrive at a more synergistic analysis of temporal data.

Additionally, other methods can be derived as further described below.

When a new image is acquired, such as image 202, the image can be processed by VCAR 204. In parallel, the newly acquired image can be registered with a previously stored image and the registered previous image can be processed by VCAR 214. The images processed by VCAR 204 and VCAR 214 can be temporally compared and visualized to provide an improved temporal comparison. See FIG. 7 for further details.

In another example, images from two different time instances are VCAR processed and the results are book marked. The book marked results are registered prior to temporal comparison. In this case, image-to-image registration is not needed. See FIG. 8 for further details.

System 200 provides three-dimensional (3D) quantification of brain aneurysms for the purpose of surgical planning and the corresponding evaluation study. System 200 uses implicit deformable models combined with non-parametric statistical information to quantify aneurysm morphology and to obtain clinically relevant parameters. System 200 supports computerized surgical planning of coiling procedures by allowing more accurate and truly 3D quantification of brain aneurysms.

System level overviews of the operation of implementations are described above in this section of the detailed description. Some implementations of system 100 and system 200 operate in a multi-processing, multi-threaded operating environment on a computer.

Method Implementations

In the previous section, a system level overview of the operation of an implementation is described. In this section, the particular methods of such an implementation are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. Methods 300-1300 are performed by a program executing on, or performed by firmware or hardware that is a part of, a computer.

Figure 3:
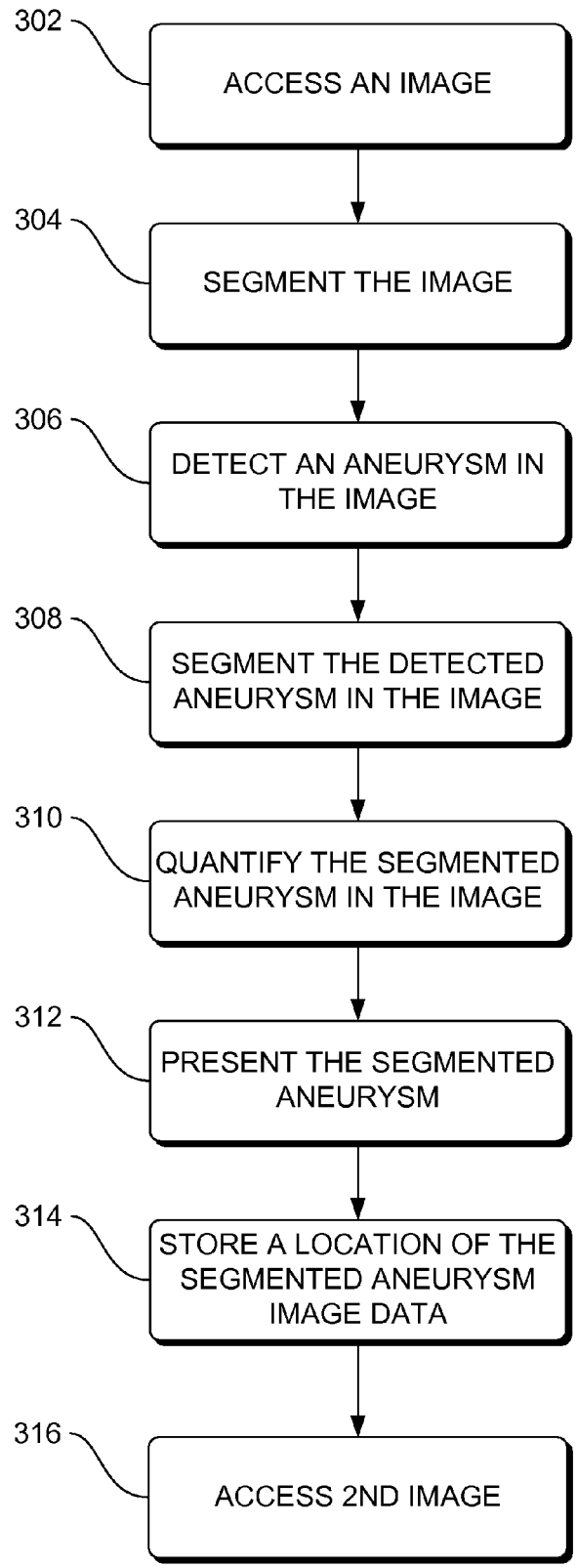
FIG. 3 is a flowchart of a method to determine changes of an anatomical structure in a patient over time, according to an implementation.

FIG. 3 is a flowchart of a method 300 to determine changes of an anatomical structure in a patient over time, according to an implementation.

Method 300 includes accessing an image in a memory, at block 302.

Some implementations of method 300 include segmenting a portion of the image containing an aneurysm, at block 304. Some implementations of the segmenting at block 304 include eliminating unwanted data in the image. Other implementations of the segmenting at block 304 include generating a mask that excludes unwanted data in the image.

Some implementations of method 300 include detecting the aneurysm in the segmented portion of the image, at block 306. Some implementations of detecting the aneurysm at block 306 include detecting an aneurysm in the image while excluding unwanted data in the image. Other implementations of detecting the aneurysm at block 306 include detecting an aneurysm in the image in reference to a mask that excludes unwanted data in the image.

Some implementations of method 300 include segmenting the detected aneurysm in the image, at block 308.

Some implementations of method 300 include quantifying the segmented detected aneurysm in the image, at block 310. In some implementations of method 300, the detecting of the aneurysm at block 306, the segmenting of the detected aneurysm at block 308 and quantifying the segmented detected aneurysm at block 310 are all performed simultaneously.

Some implementations of method 300 include visually presenting the segmented detected aneurysm, at block 312.

Some implementations of method 300 include storing a location of the segmented detected aneurysm image data to the memory, at block 314.

Some implementations of method 300 include accessing a second image in the memory, at block 316.

Figure 4:
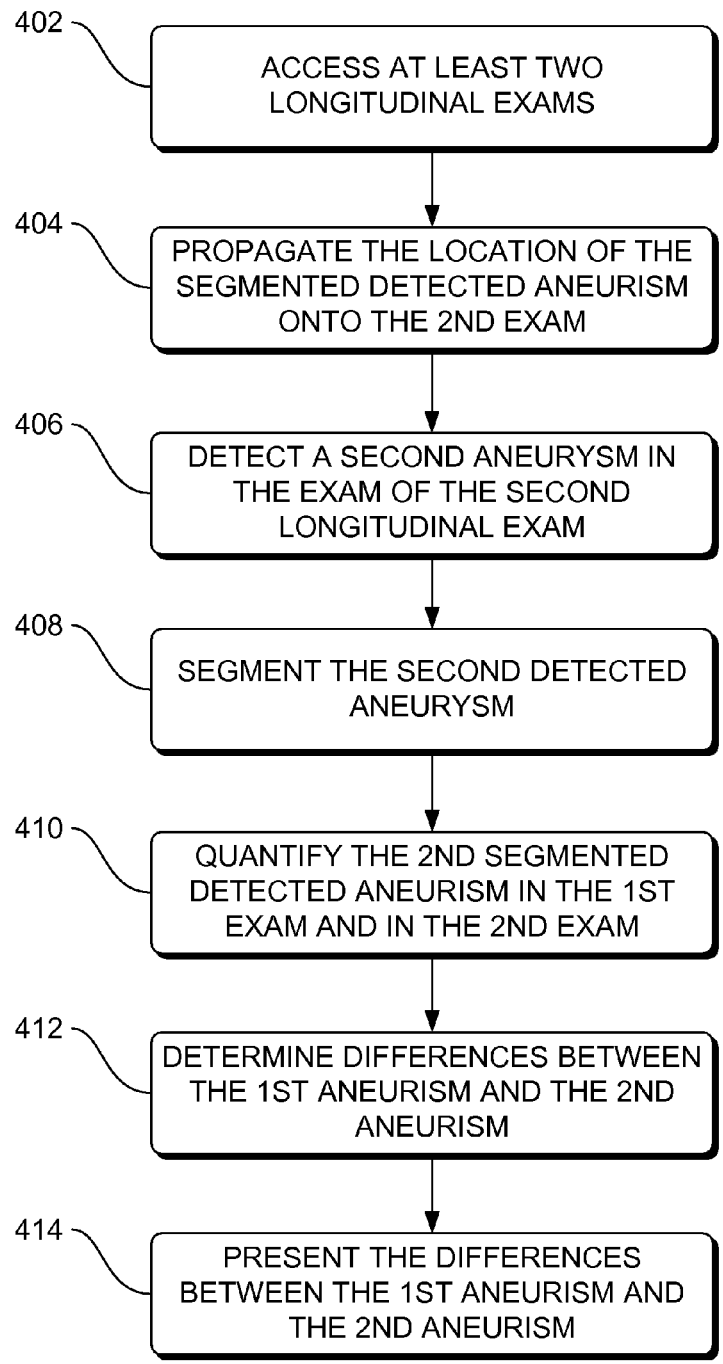
FIG. 4 is a flowchart of a method to determine changes of an anatomical structure in a patient over time, according to an implementation.

FIG. 4 is a flowchart of a method 400 to determine changes of an anatomical structure in a patient over time, according to an implementation.

Method 400 includes accessing a second image in a memory, at block 402. The first longitudinal exam has a representation of a segmented aneurysm at a location in the image and propagating a location of the segmented detected aneurysm onto the second image using bookmarking or registration, at block 404.

Some implementations of method 400 also include segmenting a second detected aneurysm in the second image, at block 406.

Some implementations of method 400 also include quantifying the second segmented detected aneurysm in the second image, at block 408. Some implementations of method 400 also include segmenting the second detected aneurysm in the image of the second longitudinal exam, at block 410. Some implementations of method 400 also include determining differences between the first segmented aneurysm and the second segmented aneurism, at block 412.

Some implementations of method 400 also include visually presenting the differences between the first segmented detected aneurysm and the second segmented detected aneurism, at block 414.

Some implementations of method 400 also include bookmarking the results of the detection and registering the bookmarked results before determining the differences.

Figure 5:
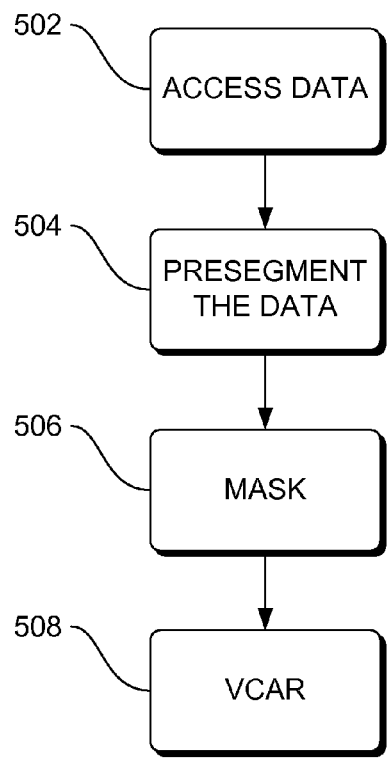
FIG. 5 is a flowchart of a method to determine changes of an anatomical structure in a patient over time, according to an implementation.

FIG. 5 is a flowchart of a method 500 to determine changes of an anatomical structure in a patient over time, according to an implementation.

Some implementations of method 500 include accessing data, at block 502. Some implementations of method 500 include pre-segmenting the data, at block 504.

Some implementations of method 500 also include masking the pre-segmented data, at block 506.

Some implementations of method 500 also include processing of the masked data by a volume computer-assisted reading (VCAR) detector (e.g. VCAR 204 in FIG. 2), at block 508.

Figure 6:
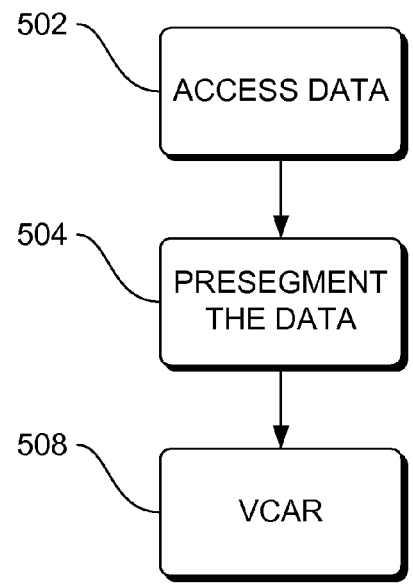
FIG. 6 is a flowchart of a method to determine changes of an anatomical structure in a patient over time, according to an implementation.

FIG. 6 is a flowchart of a method 600 to determine changes of an anatomical structure in a patient over time, according to an implementation.

Some implementations of method 600 include accessing data, at block 502. Some implementations of method 600 include pre-segmenting the data, at block 504.

Some implementations of method 600 also include processing of the pre-segmented data by a volume computer-assisted reading (VCAR) detector (e.g. VCAR 204 in FIG. 2, at block 602.

Figure 7:
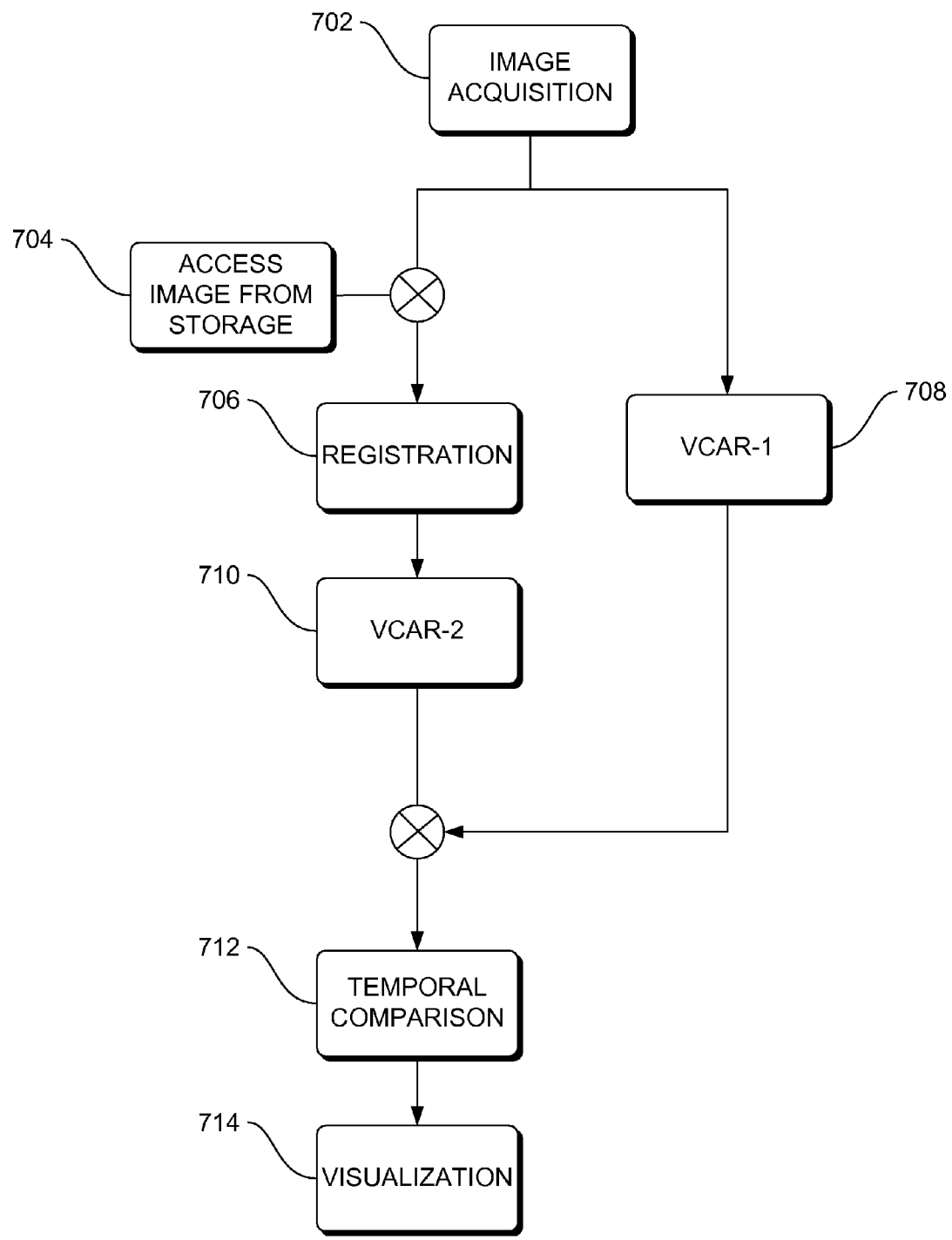
FIG. 7 is a flowchart of a method to determine changes of an anatomical structure in a patient over time, in which results are registered prior to processing by a VCAR so that the results are in the co-registered space, according to an implementation.

FIG. 7 is a flowchart of a method 700 to determine changes of an anatomical structure in a patient over time, in which results are registered prior to processing by a VCAR so that the results are in the co-registered space, according to an implementation.

Some implementations of method 700 include acquisition of an image, at block 702.

In some implementations of 700, the acquired image is stored in a nonvolatile storage, such as an acquisition module, and thereafter accessed, at block 704. The acquisition storage module stores acquired or synthesized images. For temporal change analysis, means are provided to retrieve the data from storage corresponding to an earlier time point. To simplify notation in the subsequent discussion we describe only two images to be compared, even though the general approach can be extended for any number of images in the acquisition and temporal sequence. Let S1 and S2 be the two images to be registered and compared.

The accessed image is registered at block 706 and processed by a volume computer-assisted reading (VCAR) detector (e.g. VCAR 204 in FIG. 2).

Subsequently a second image is acquired, at block 702, and the second image is processed by a volume computer-assisted reading (VCAR) detector (e.g. VCAR 204 in FIG. 2), at block 710. Thereafter, a temporal comparison is performed on the first registered image in the second image, at block 712. The temporal comparison at block 712 identifies changes of an anatomical structure in a patient over time.

Thereafter, the changes in the anatomical structure in the patient over time are visualized, at block 714.

Figure 8:
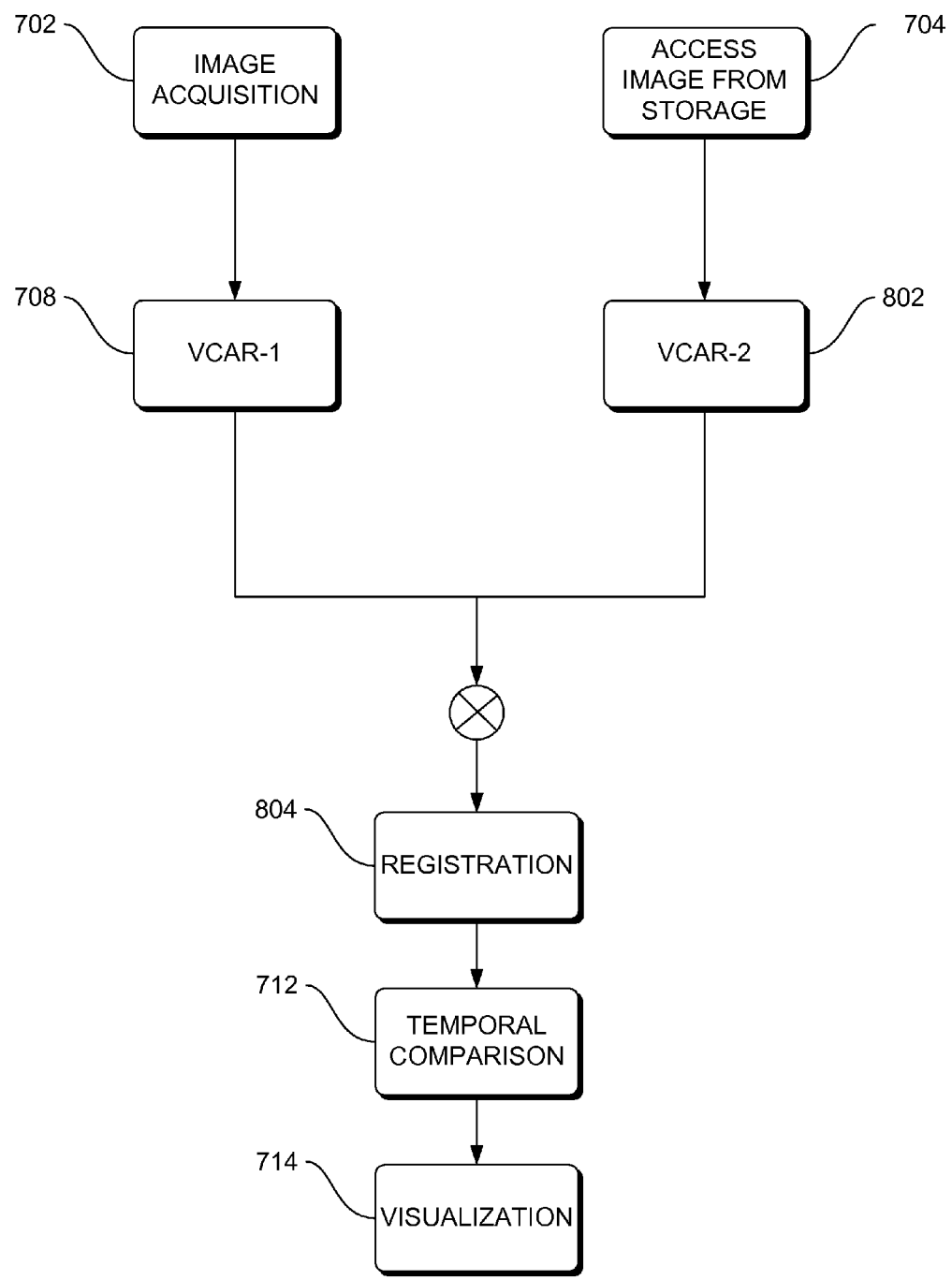
FIG. 8 is a flowchart of a method to determine changes of an anatomical structure in a patient over time, in which VCAR results are bookmarked and registered prior to temporal comparison, according to an implementation.

FIG. 8 is a flowchart of a method 800 to determine changes of an anatomical structure in a patient over time, in which VCAR results are bookmarked and registered prior to temporal comparison, according to an implementation.

Method 800 includes acquisition of a first image, at block 702. The first image is processed by a volume computer-assisted reading (VCAR) detector (e.g. VCAR 204 in FIG. 2), at block 708.

A second image in storage is accessed, at block 704. The second image is processed by a VCAR detector, at block 710.

Subsequently, the two VCAR-processed images are registered, and block 804. Thereafter, a temporal comparison is performed on the first registered image in the second image, at block 712. The temporal comparison at block 712 identifies changes of an anatomical structure in a patient over time. In method 700, image-to-image registration is not needed.

Thereafter, in some implementations, the changes in the anatomical structure in the patient over time are visualized, at block 714.

Figure 9:
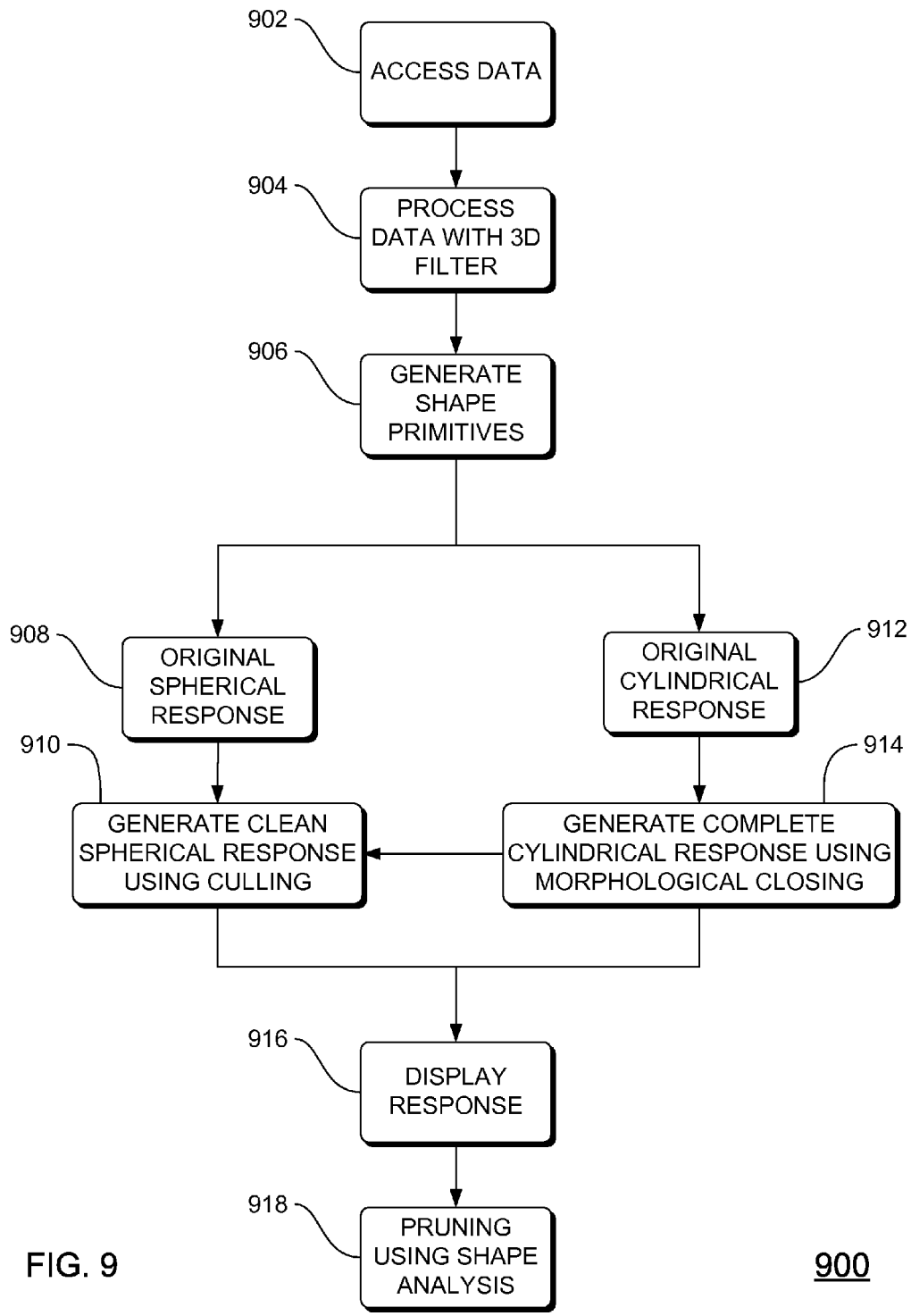
FIG. 9 is a flowchart of a method of spherical shape determination, according to an implementation.

FIG. 9 is a flowchart of a method 900 of spherical shape determination, according to an implementation.

Method 900 includes acquiring at block 902, at least two images. Examples of the images include image 102 and image 112.

Method 900 also includes processing the plurality of images with a three-dimensional (3D) filter, at block 904. Thereafter, shape primitives are generated from the processed data, at block 906.

In method 900, an original spherical response is generated from the shape primitives, at block 908. Thereafter a complete spherical response (should that be "clean response") is generated from the original spherical response using culling, at block 910. Action 910 is performed by culling responses that overlap with the complete cylindrical response.

In method 900, an original cylindrical response is generated from the shape primitives, at block 912. Thereafter a complete cylindrical response (should that be "clean response") is generated from the original cylindrical response using morphological closing, at block 914. Action 914 is based on anatomy and acquisition parameters.

Subsequently method 900 includes displaying the responses generated at block 912 and block 916. In some implementations method 900 also includes pruning the spherical responses using shape analysis, at block 918.

Figure 10:
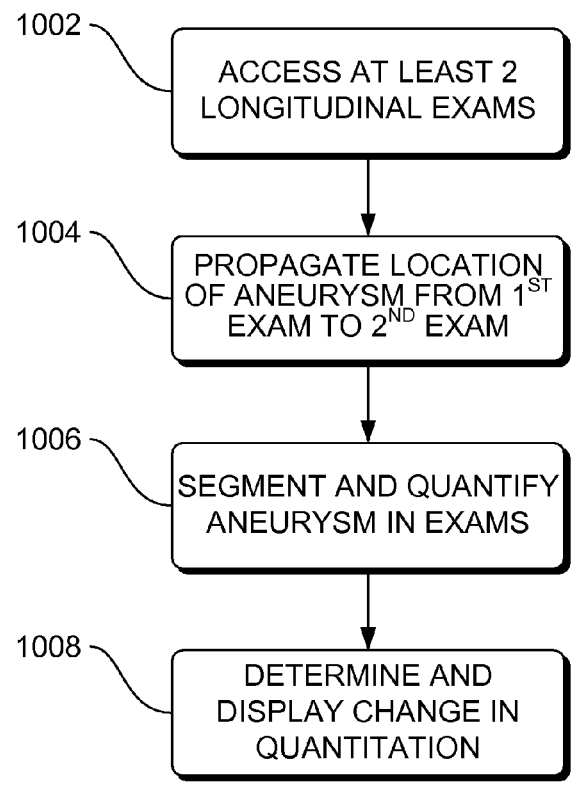
FIG. 10 is a flowchart of a method of longitudinal analysis, according to an implementation.

FIG. 10 is a flowchart of a method 1000 of longitudinal analysis, according to an implementation.

Method 1000 includes accessing at least two longitudinal exams, at block 1002. In action 1002, two exams that were acquired at significantly different times for a meaningful change assessment of the anomaly, i.e. aneurysm, are accessed. A key element of this action is the loading of the stored location of the aneurysm from the earlier exam. This action involves loading of data at time instance $t_1$ and at least at time instance $t_2$, as well as loading the location (with other attributes) of all aneurysms at time instance $t_1$.

Method 1000 also includes propagating at least one location of an aneurysm from a first exam of the longitudinal exams to a second exam of the longitudinal exams, at block 1004. The propagation of locations 1004 involves the automatic propagation of the aneurysm location from the exam at time instance $t_1$ to time instance $t_2$, which is accomplished by a registration of the two datasets so that the locations are propagated in an accurate manner. Some implementations provide an option for a user to interact with the propagated locations and perform adjustments if needed.

Method 1000 also includes segmenting and quantifying the aneurysm at the location, at block 1006. Segmentation and quantification of aneurysms in both exams at the validated location determine the volume (and other properties, like texture, shape, etc.) of the aneurysms at both time instances $t_1$ and $t_2$. Method 100 is not affected by changes occurring in non-aneurysm areas and the results are targeted toward only aneurysm like shapes.

Thereafter method 1000 also includes determining and displaying at least one change in quantitation of the aneurysm, at block 1008. There are several quantifications that can be done including but not limited to determining number of clusters, area, path, shape, size, boundary, volume, location, statistics, skeleton etc. The change in size and/or appearance of the aneurysm from time $t_1$ to time $t_2$ is displayed to the user so that the user can make an assessment for the next course of action.

Figure 11:
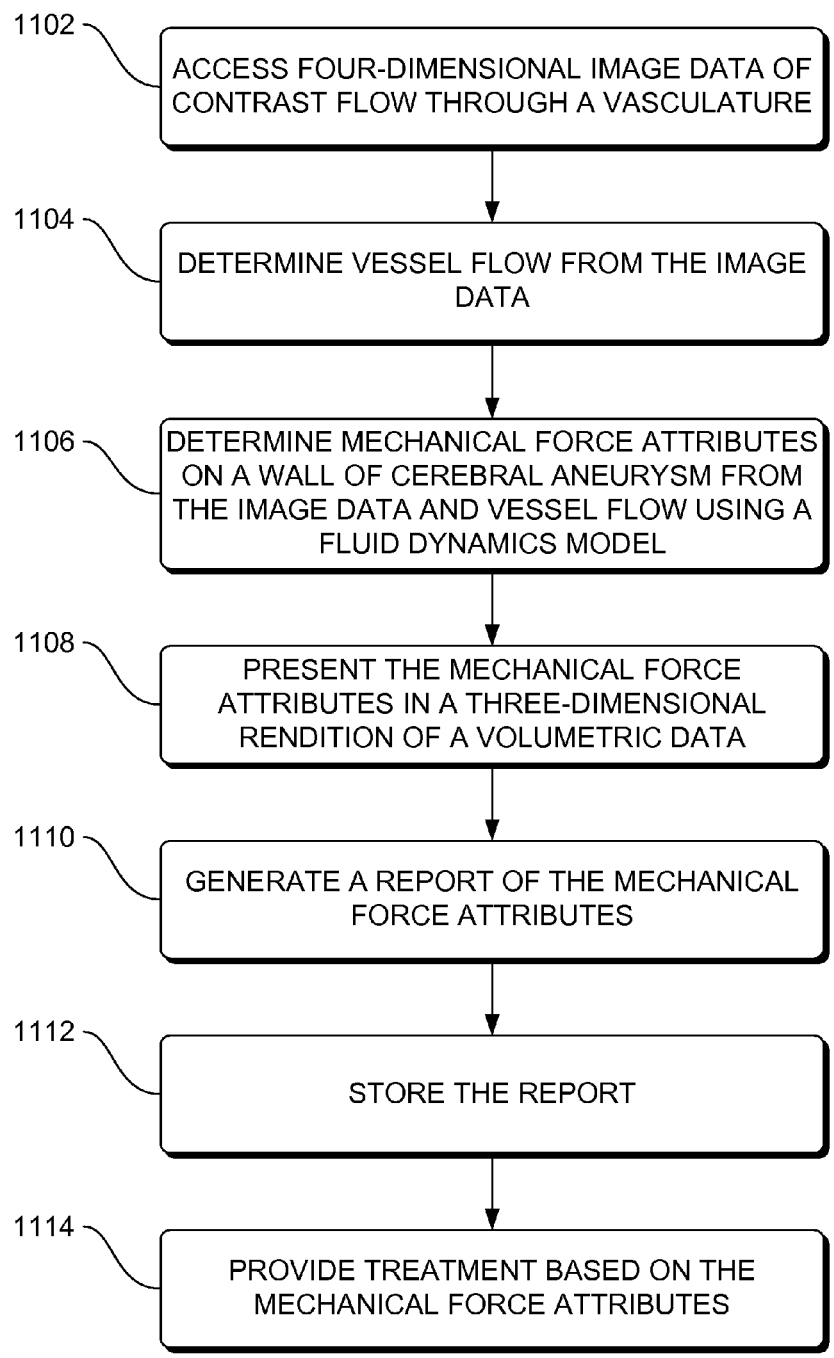
FIG. 11 is a flowchart of a method to image a patient, according to an implementation.

FIG. 11 is a flowchart of a method 1100 to image a patient, according to an implementation.

Figure 12:
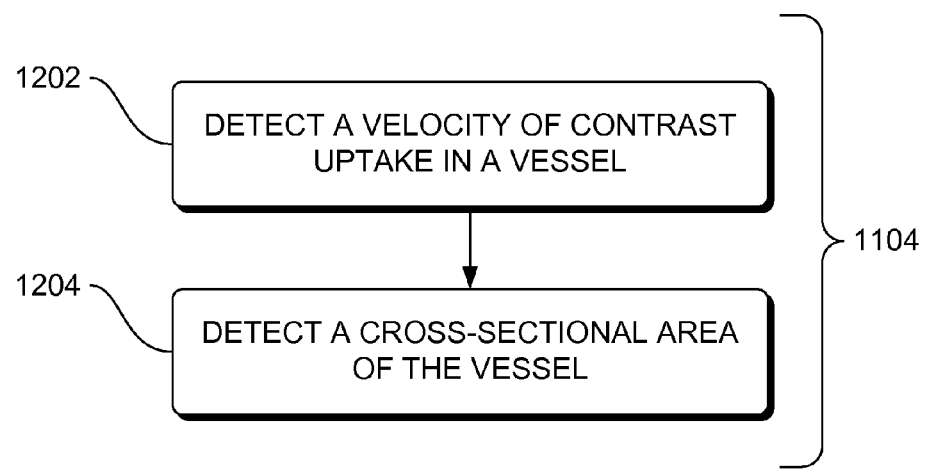
FIG. 12 is a flowchart of a method to determine vessel flow information, according to an implementation.

Method 1100 includes accessing four-dimensional image data that tracks and/or describes contrast flow through a vasculature, at block 1102. Method 1100 also includes determining vessel flow information of the vasculature from the four-dimensional image data, at block 1104. One implementation of determining vessel flow information at block 1104 is shown in FIG. 12 below.

Method 1100 also includes determining mechanical force attributes (e.g. stress and strain) on a wall of an aneurism, at block 1106. The mechanical force attributes are determined from the vessel flow information using a fluid dynamics model in which the mechanical force attributes varies in proportion (e.g. linearly) to a velocity of fluid in a proximity to a location in the vasculature in a direction that is perpendicular to a plane of shear in the vasculature. Method 1100 also includes visually presenting the determined mechanical force attributes in three-dimensional rendition of the volumetric data using visual cues to indicate a degree of mechanical force attributes, at block 1108.

Some implementations of method 1100 also include generating a report of the determined mechanical force attributes, at block 1110 and then storing the report, at block 1112.

Some implementations of method 1100 also include determining and/or providing treatment based on the determined mechanical force attributes, at block 1114.

FIG. 12 is a flowchart of a method 1200 to determine vessel flow information, according to an implementation. Method 1200 is one example of determining vessel flow information at block 1104 in FIG. 11.

Figure 13:
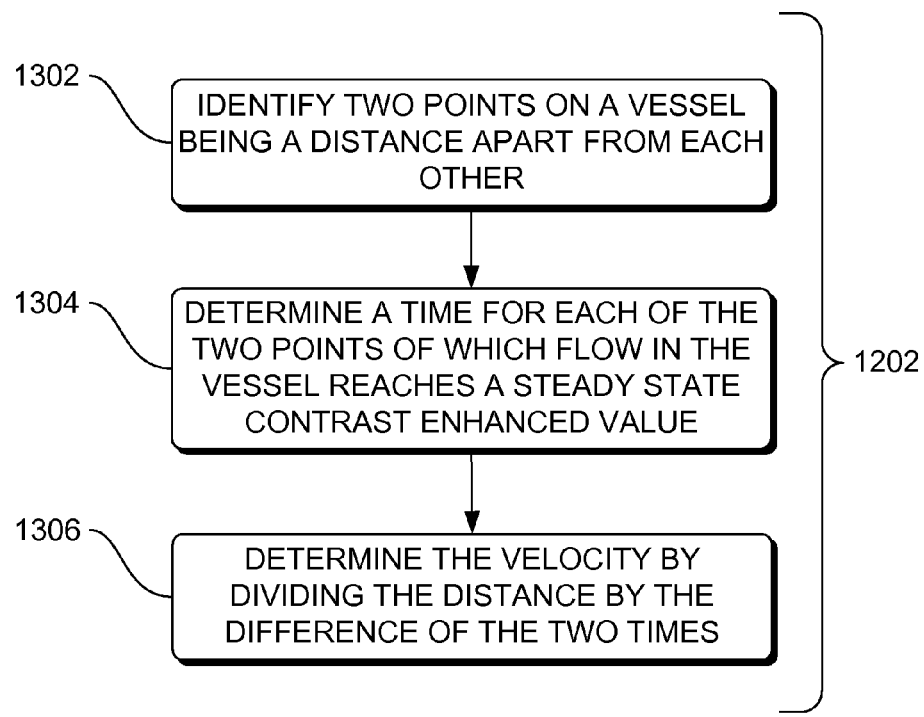
FIG. 13 is a flowchart of a method to determine vessel flow information, according to an implementation.

Method 1200 includes detecting a velocity of contrast uptake in a vessel, at block 1202. One example of detecting the velocity of contrast uptake in the vessel at block 1202 is shown in FIG. 13. Method 1200 also includes detecting a cross-sectional area of the vessel, at block 1204.

FIG. 13 is a flowchart of a method 1300 to determine vessel flow information, according to an implementation. Method 1300 is one example of detecting velocity of contrast uptake in a vessel, at block 1202 in FIG. 12.

Method 1300 includes identifying two points on a vessel being a distance apart from each other, at block 1302. Method 1300 also includes determining a time for each of the two points of which flow in the vessel reaches a steady state contrast enhanced value, at block 1304.

Method 1300 also includes determining the velocity by dividing the distance by the difference of the two times, at block 1306.

In some implementations, methods 300-1300 are implemented as a computer data signal embodied in a carrier wave, that represents a sequence of instructions which, when executed by a processor, such as a processor, cause the processor to perform the respective method. In other implementations, methods 300-1300 are implemented as a computer-accessible medium having executable instructions capable of directing a processor to perform the respective method. In varying implementations, the medium is a magnetic medium, an electronic medium, or an optical medium.

The following description provides an overview of computer hardware and a suitable computing environment in conjunction with which some implementations can be implemented. Implementations are described in terms of a computer executing computer-executable instructions. However, some implementations can be implemented entirely in computer hardware in which a computer-executable instructions are implemented in read-only memory. Some implementations can also be implemented in client/server computing environments where remote devices that perform tasks are linked through a communications network. Program modules can be located in both local and remote memory storage devices in a distributed computing environment.

The aspects of class hierarchy 500 and use cases 600, 700, 800, 900, 1000, 1100, 1200 and 1300 shown in FIG. 5-13 can be embodied as computer hardware circuitry or as a computer-readable program, or a combination of both. In other aspects, the systems and method described herein are implemented in an application service provider (ASP) system.

More specifically, in the computer-readable program aspect, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 1500 in FIG. 15, or on at least as many computers as there are components.

Figure 14:
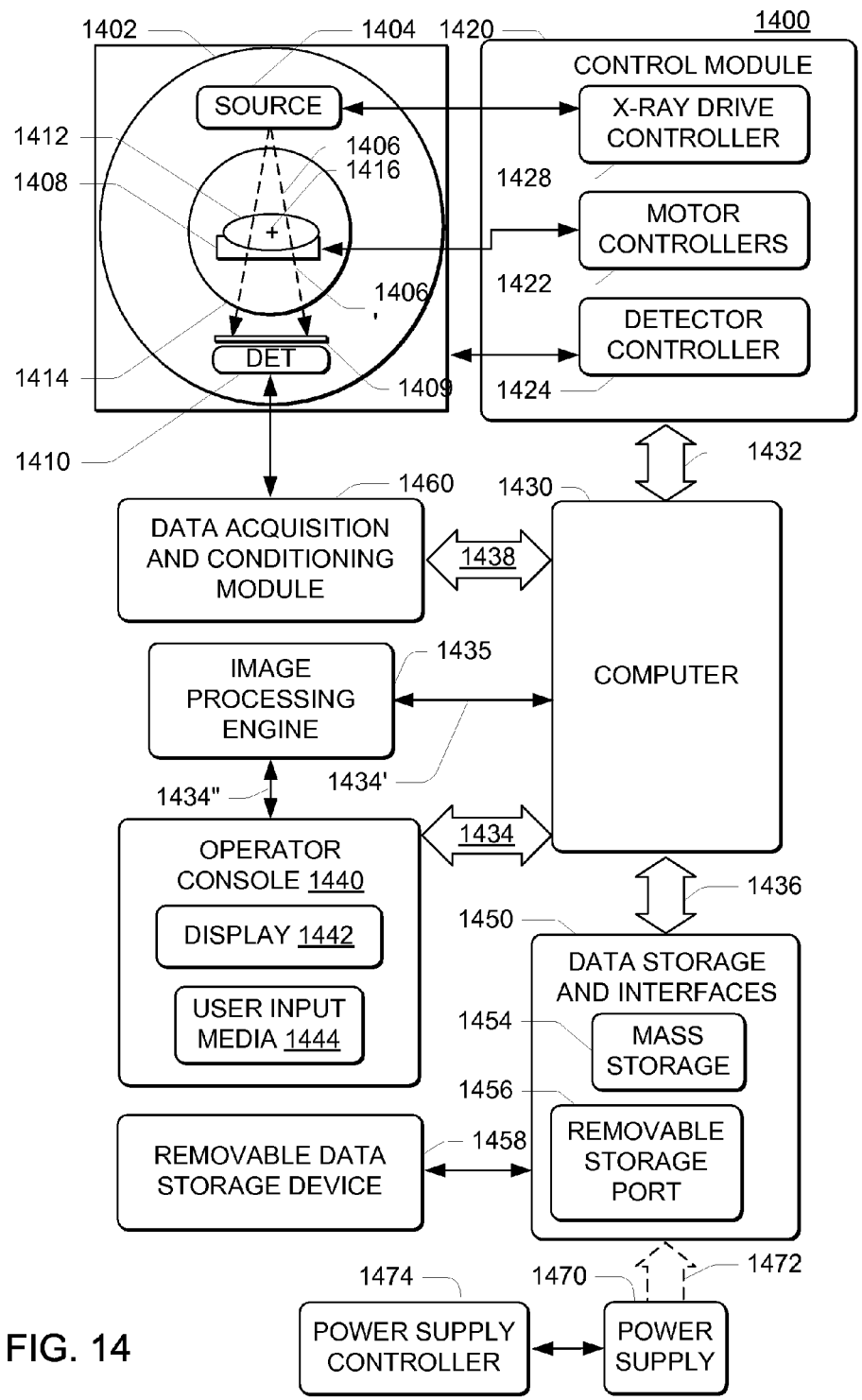
FIG. 14 is a simplified diagram of an overview of a modified system configured to improve X-ray imaging operations.

FIG. 14 is a simplified diagram of an overview of a modified system 1400 configured to improve X-ray imaging operations. The system 1400 optionally includes a gantry 1402 or other support for an illumination source 1404, such as an X-ray illumination source, capable of providing illumination 1406, such as X-rays or other non-destructive internal imaging illumination, and can optionally include a test subject support 1408 that is transmissive with respect to the illumination 1406 and that is positioned above a scintillator 1409 and detector 1410 that is also opposed to the illumination source 1404. Alternatively, a direct conversion detector 1410 can be employed without need for a scintillator.

In one aspect, components of the system 1400 and a test subject 1412 are maintained in a defined geometric relationship to one another by the gantry 1402. A distance between the illumination source 1404 and the detector 1410 can be varied, depending on the type of examination sought, and the angle of the illumination 1406 respective to the test subject 1412 can be adjusted with respect to the body to be imaged responsive to the nature of imaging desired.

In one aspect, the test subject support 1408 is configured to support and/or cause controlled motion of the test subject 1412, such as a living human or animal patient, or other test subject 1412 suitable for non-destructive imaging, above the scintillator 1409/detector 1410 so that illumination 1407 is incident thereon after passing through the test subject 1412. In turn, information from the detector array 1410 describes internal aspects of the test subject 1412.

The scintillator 1409 can be a conventional CsI scintillator 1409, optically coupled to an array of photodiodes (not illustrated), such as a two-dimensional array of photodiodes and suitable control transistors formed using semiconductor material such as amorphous silicon, or any other form of detector 1410 suitable for use with the type or types of illumination 1406 being employed, such as X-rays. The detector elements are typically tesselated in a mosaic. The scintillator 1409 converts incident photons comprising electromagnetic radiation, such as X-rays, from high-energy, high-frequency photons 1407, into lower-energy, lower-frequency photons corresponding to spectral sensitivity of the detector elements, in a fashion somewhat analogous to fluorescence, as is commonly known in the context of many visible-light sources in use today. Alternatively, the detector 1410 can be formed as a flat-panel array including amorphous Silicon ($\alpha$-Si) active elements, together with either a scintillator layer 1409, or a direct converter material such as Cadmium Zinc Telluride (CdZnTe), Mercuric Iodide ($HgI_2$), Lead Iodide ($PbI_2$), or amorphous Selenium ($\alpha$-Se).

In some modes of operation, such as CT, the gantry 1402 and test subject support or table 1408 cooperatively engage to move the test subject 1412 longitudinally within an opening 1414, that is, along an axis 1416 extending into and out of the plane of FIG. 14. In some modes of operation, the gantry 1402 rotates the X-ray source 1404 and detector 1410 about the axis 1416, while the support 1408 moves longitudinally, to provide a helical series of scans of the test subject 1412, where a pitch of the helices is defined as a ratio of a longitudinal distance traveled by the table 1408 during a complete revolution of the gantry 1402, compared to a length of the detector 1410 along the axis 1416 of linear motion.

The system 1400 also optionally includes a control module or controller 1420. The controller 1420 can include a motor control module 1422 configured to move the test subject support 1408 and thus the test subject 1412 relative to the X-ray source 1404 and/or detector 1410, and can also control motors in the gantry 1402 or to position the X-ray illumination source 1404 relative to the test subject 1412 and/or the detector 1410.

The controller 1420 includes a detector controller 1424 configured to control elements within the detector 1410 and to facilitate data transfer therefrom. The controller 1420 also includes a drive parameter controller 1428 configured to control electrical drive parameters delivered to the X-ray source 1404. One or more computers 1430 provide connections to the controller 1420 via a bus 1432 configured for receiving data descriptive of operating conditions and configurations and for supplying appropriate control signals. Buses 1434, 1437 and 1439 act to transfer data and control signals, for example with respect to a module 1435, configured as an image processing engine, via interconnections such as 1437, 1439 that are configured for exchange of signals and data to and/or from the computer 1430 as well as other elements of the system 1400 and/or external computation or communications resources (not illustrated in FIG. 14).

The system 1400 also includes a bus 1436, a bus 1438 and an operator console 1440. The operator console 1440 is coupled to the system 1400 through the bus 1434. The operator console 1440 includes one or more displays 1442 and a user input interface 1444. The user input interface 1444 can include a touchscreen, keyboard, a mouse or other tactile input device, capability for voice commands and/or other input devices. The one or more displays 1442 provide video, symbolic and/or audio information relative to operation of system 1400, user-selectable options and images descriptive of the test subject 1412, and can display a graphical user interface for facilitating user selection among various modes of operation and other system settings.

The image processing engine 1435 facilitates automation of accurate measurement and assessment. The image processing engine 1435 is capable of forming multiple, coordinated images for display, for example via the monitor 1442, to provide the types of depictions described below. The image processing engine 1435 can comprise a separate and distinct module, which can include application-specific integrated circuitry, or can comprise one or more processors coupled with suitable computer-readable program modules, or can comprise a portion of the computer 1430 or other computation device.

The system 1400 also includes memory devices 1450, coupled via the bus 1436 to the computer 1430 through suitable interfaces. Datasets representing three-dimensional data and image or two-dimensional data typically conform to the digital imaging and communications in medicine (DICOM) standard, which is widely adopted for handling, storing, printing, and transmitting information in medical imaging. The DICOM standard includes a file format definition and a network communications protocol. The communication protocol is an application protocol that uses TCP/IP to communicate between systems. DICOM files can be stored in memory devices 1450 and retrieved therefrom, and can be exchanged between two entities that are capable of receiving image and patient data in DICOM format.

The memory devices 1450 include mass data storage capabilities 1454 and one or more removable data storage device ports 1456. The one or more removable data storage device ports 1456 are adapted to detachably couple to portable data memories 1458, which can include optical, magnetic and/or semiconductor memories and can have read and/or write capabilities, and which can be volatile or non-volatile devices or can include a combination of the preceding capabilities.

The system 1400 further includes a data acquisition and conditioning module 1460 that has data inputs coupled to the detector 1410 and that is coupled by the bus 1438 to the one or more computers 1430. The data acquisition and conditioning module 1460 includes analog to digital conversion circuitry for capturing analog data from the detector 1410 and then converting those data from the detector 1410 into digital form, to be supplied to the one or more computers 1430 for ultimate display via at least one of the displays 1442 and for potential storage in the mass storage device 1454 and/or data exchange with remote facilities (not shown in FIG. 14). The acquired image data can be conditioned in either the data acquisition and conditioning module 1460 or the one or more computers 1430 or both.

The system 1400 also includes a power supply 1470, coupled via interconnections represented as a power supply bus 1472, shown in dashed outline, to other system elements, and a power supply controller 1474. In some aspects, the system 1400 is configured to be a mobile system equipped with a portable power supply 1470, such as a battery. In other words, the system 1400 can comprise a wheeled unit and can be electromotively powered in self-contained fashion, lending physical agility to the ensemble of attributes offered by the system 1400.

Volumetric data collected via exposure of the test subject 1412 to suitable illumination 1406 can be processed via many different types of tools, each intended to enhance some portion of the information content described by the data. One result can be inconsistency between analytical results from different types of signal processing tools, or between measurement results corresponding to different measurement times and/or measurement phases.

Figure 15:
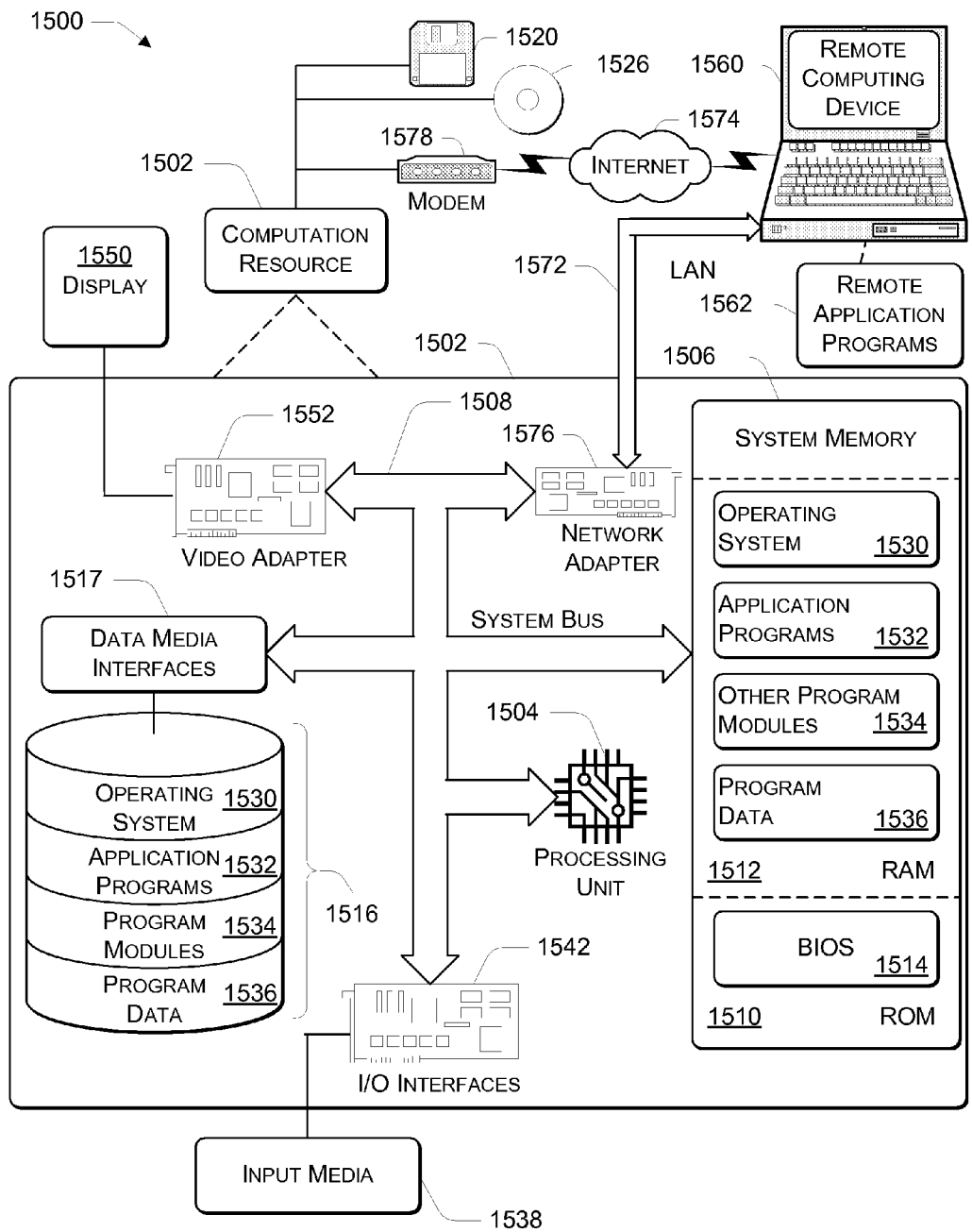
FIG. 15 illustrates an example of a general computer environment useful in the context of the environment of FIG. 14, in accordance with an aspect of the disclosed subject matter.

FIG. 15 illustrates an example of a general computer environment 1500 useful in the context of the environment of FIG. 14, in accordance with an aspect of the disclosed subject matter. The general computer environment 1500 includes a computation resource 1502 capable of implementing the processes described herein. It will be appreciated that other devices can alternatively used that include more components, or fewer components, than those illustrated in FIG. 15.

The illustrated operating environment 1500 is only one example of a suitable operating environment, and the example described with reference to FIG. 15 is not intended to suggest any limitation as to the scope of use or functionality of the aspects of this disclosure. Other well-known computing systems, environments, and/or configurations can be suitable for implementation and/or application of the subject matter disclosed herein.

The computation resource 1502 includes one or more processors or processing units 1504, a system memory 1506, and a bus 1508 that couples various system components including the system memory 1506 to processor(s) 1504 and other elements in the environment 1500. The bus 1508 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols.

The system memory 1506 includes nonvolatile read-only memory (ROM) 1602 and random access memory (RAM) 1512, which can or can not include volatile memory elements. A basic input/output system (BIOS) 1514, containing the elementary routines that help to transfer information between elements within computation resource 1502 and with external items, typically invoked into operating memory during start-up, is stored in ROM 1510.

The computation resource 1502 further can include a non-volatile read/write memory 1516, represented in FIG. 15 as a hard disk drive, coupled to bus 1508 via a data media interface 1517 (e.g., a SCSI, ATA, or other type of interface); a magnetic disk drive (not shown) for reading from, and/or writing to, a removable magnetic disk 1520 and an optical disk drive (not shown) for reading from, and/or writing to, a removable optical disk 1526 such as a CD, DVD, or other optical media.

The non-volatile read/write memory 1516 and associated computer-readable media provide nonvolatile storage of computer-readable instructions, data structures, program modules and other data for the computation resource 1502. Although the exemplary environment 1500 is described herein as employing a non-volatile read/write memory 1516, a removable magnetic disk 1520 and a removable optical disk 1526, it will be appreciated by those skilled in the art that other types of computer-readable media which can store data that is accessible by a computer, such as magnetic cassettes, FLASH memory cards, random access memories (RAMs), read only memories (ROM), and the like, can also be used in the exemplary operating environment.

A number of program modules can be stored via the non-volatile read/write memory 1516, magnetic disk 1520, optical disk 1526, ROM 1510, or RAM 1512, including an operating system 1530, one or more application programs 1532, other program modules 1534 and program data 1536. Examples of computer operating systems conventionally employed for some types of three-dimensional and/or two-dimensional medical image data include the NUCLEUS operating system, the LINUX® operating system, and others, for example, providing capability for supporting application programs 1532 using, for example, code modules written in the C++® computer programming language.

A user can enter commands and information into computation resource 1502 through input devices such as input media 1538 (e.g., keyboard/keypad, tactile input or pointing device, mouse, foot-operated switching apparatus, joystick, touchscreen or touchpad, microphone, antenna etc.). Such input devices 1538 are coupled to the processing unit 1504 through a conventional input/output interface 1542 that is, in turn, coupled to the system bus. A monitor 1550 or other type of display device is also coupled to the system bus 1508 via an interface, such as a video adapter 1552.

The computation resource 1502 can include capability for operating in a networked environment (as illustrated in FIG. 14, for example) using logical connections to one or more remote computers, such as a remote computer 1560. The remote computer 1560 can be a personal computer, a server, a router, a network PC, a peer device or other common network node, and typically includes many or all of the elements described above relative to the computation resource 1502. In a networked environment, program modules depicted relative to the computation resource 1502, or portions thereof, can be stored in a remote memory storage device such as can be associated with the remote computer 1560. By way of example, remote application programs 1562 reside on a memory device of the remote computer 1560. The logical connections represented in FIG. 15 can include interface capabilities, e.g., such as interface capabilities 1452 (FIG. 14) a storage area network (SAN, not illustrated in FIG. 15), local area network (LAN) 1572 and/or a wide area network (WAN) 1574, but can also include other networks.

In certain aspects, the computation resource 1502 executes an Internet Web browser program (which can optionally be integrated into the operating system 1530), such as the "Internet Explorer®" Web browser manufactured and distributed by the Microsoft Corporation of Redmond, Wash.

When used in a LAN-coupled environment, the computation resource 1502 communicates with or through the local area network 1572 via a network interface or adapter 1576. When used in a WAN-coupled environment, the computation resource 1502 typically includes interfaces, such as a modem 1578, or other apparatus, for establishing communications with or through the WAN 1574, such as the Internet. The modem 1578, which can be internal or external, is coupled to the system bus 1508 via a serial port interface.

In a networked environment, program modules depicted relative to the computation resource 1502, or portions thereof, can be stored in remote memory apparatus. It will be appreciated that the network connections shown are exemplary, and other means of establishing a communications link between various computer systems and elements can be used.

A user of a computer can operate in a networked environment 1400 using logical connections to one or more remote computers, such as a remote computer 1560, which can be a personal computer, a server, a router, a network PC, a peer device or other common network node. Typically, a remote computer 1560 includes many or all of the elements described above relative to the computer 1500 of FIG. 15.

The computation resource 1502 typically includes at least some form of computer-readable media. Computer-readable media can be any available media that can be accessed by the computation resource 1502. By way of example, and not limitation, computer-readable media can comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computation resource 1502.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media include wired media, such as wired network or direct-wired connections, and wireless media, such as acoustic, RF, infrared and other wireless media. The scope of the term computer-readable media includes combinations of any of the above.

The computer 1502 can function as one or more of the control segments of module 1420 (FIG. 14), the computer 1430, the operator console 1440 and/or the data acquisition and conditioning module 1460, for example, via implementation of the process 200 FIG. 2, respectively, as one or more computer program modules.

CONCLUSION

An aneurysm imaging system is described. A technical effect is temporal comparison of aneurysm in longitudinal exams. Although specific implementations have been illustrated and described herein, it will be appreciated by those of ordinary skill in the art that any arrangement which is calculated to achieve the same purpose may be substituted for the specific implementations shown. This application is intended to cover any adaptations or variations. For example, although described in procedural terms, one of ordinary skill in the art will appreciate that implementations can be made in an object-oriented design environment or any other design environment that provides the required relationships.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future communication devices, different file systems, and new data types.

The terminology used in this application is meant to include all imaging, database and communication environments and alternate technologies which provide the same functionality as described herein.

We claim:

1. A method to image a patient, the method comprising:
    accessing four-dimensional image data that tracks a flow of a previously injected contrast agent through a vasculature;
    determining vessel flow information of the vasculature;
    determining mechanical force attributes on a wall of an aneurysm from the vessel flow information using a fluid dynamics model wherein the mechanical force attributes vary in proportion to velocity of fluid in the vasculature in a direction perpendicular to a plane of shear in the vasculature;
    generating a three-dimensional image of the vasculature using the four-dimensional image data; and
    visually presenting the determined mechanical force attributes in the three-dimensional image using visual cues to indicate degree of mechanical force attributes.

2. The method of claim 1, wherein the fluid dynamics model further comprises:
    a Navier-Stokes fluid dynamics model.

3. The method of claim 1, wherein the accessing further comprises:
    accessing four-dimensional data that tracks contrast flow through a vasculature.

4. The method of claim 1, wherein the determining vessel flow information further comprises:
    detecting a velocity of contrast uptake in a vessel; and
    detecting a cross-sectional area of the vessel.

5. The method of claim 1, wherein the determining vessel flow information further comprises:
    identifying two points on a vessel being a distance apart from each other;
    determining a time for each of the two points of which flow in the vessel reaches a steady state contrast enhanced value; and
    determining the velocity by dividing the distance by the difference of the two times.

6. The method of claim 1, further comprising:
    generating a report of the determined mechanical force attributes; and
    storing the report.

7. The method of claim 1, further comprising:
    providing treatment based on the determined mechanical force attributes.

8. A non-transitory computer-accessible medium having executable instructions to image a patient, the executable instructions capable of directing a processor to perform:
    determining mechanical force attributes on a wall of an aneurysm using a fluid dynamics model; and
    visually presenting the determined mechanical force attributes in three-dimensional rendition of the volumetric data using visual cues to indicate degree of mechanical force attributes.

9. The non-transitory computer-accessible medium of claim 8, wherein the fluid dynamics model further comprises:
    a Navier-Stokes fluid dynamics model.

10. The non-transitory computer-accessible medium of claim 8, wherein the mechanical force attributes further comprises:
linearly proportional to velocity of fluid in a proximity to a location in a direction perpendicular to a plane of shear in the location.

11. The non-transitory computer-accessible medium of claim 8, the medium further comprising executable instructions capable of directing the processor to perform:
accessing four-dimensional image data that describes a contrast flow, of a previously injected contrast agent, through a vasculature; and
determining vessel flow information.

12. The non-transitory computer-accessible medium of claim 11, wherein the executable instructions capable of directing the processor to perform the accessing further comprise executable instructions capable of directing the processor to perform:
accessing four-dimensional image data that describes contrast flow through a vasculature.

13. The non-transitory computer-accessible medium of claim 11, wherein the executable instructions capable of directing the processor to perform the determining vessel flow information further comprise executable instructions capable of directing the processor to perform:
detecting a velocity of contrast uptake in a vessel; and
detecting a cross-sectional area of the vessel.

14. The non-transitory computer-accessible medium of claim 13, wherein the executable instructions capable of directing the processor to perform the determining vessel flow information further comprise executable instructions capable of directing the processor to perform:
identifying two points on a vessel being a distance apart from each other;
determining a time for each of the two points of which flow in the vessel reaches a steady state contrast enhanced value; and
determining the velocity by dividing the distance by the difference of the two times.

15. The non-transitory computer-accessible medium of claim 8 further comprising executable instructions capable of directing the processor to perform:
generating a report of the determined mechanical force attributes; and
storing the report.

16. The non-transitory computer-accessible medium of claim 8 further comprising executable instructions capable of directing the processor to perform:
providing treatment based on the determined mechanical force attributes.

17. A medical imaging system comprising:
a processor;
a storage device coupled to the processor;
software apparatus operable on the processor comprising:
a fluids dynamics model;
a vessel flow analyzer operable to determine vessel flow data of a vasculature represented in four-dimensional image data; and
a mechanical force analyzer that is operable to determine a mechanical force attributes on a wall of an aneurysm from the vessel flow data using the fluid dynamics model wherein the mechanical force attributes varies in proportion to a velocity of a fluid in the vasculature in a direction perpendicular to a plane of shear in the vasculature;
wherein an apparatus operable to visually display the mechanical force attributes in three-dimensional rendition of the volumetric data using visual cues to indicate a degree of mechanical force attributes.

18. The medical imaging system of claim 17, wherein the fluid dynamics model further comprises:
a Navier-Stokes fluid dynamics model.

19. The medical imaging system of claim 17, wherein the four-dimensional image data further comprises:
four-dimensional image data.

* * * * *